United States Patent
Massingill

(10) Patent No.: US 10,526,299 B2
(45) Date of Patent: Jan. 7, 2020

(54) FIBER CONDUIT REACTOR WITH A HEAT EXCHANGE MEDIUM INLET AND A HEAT EXCHANGE MEDIUM OUTLET

(71) Applicant: Chemtor, LP, San Marcos, TX (US)

(72) Inventor: John Lee Massingill, San Marcos, TX (US)

(73) Assignee: Chemtor, LP, San Marcos, TX (US)

( * ) Notice: Subject to any disclaimer, the term of this patent is extended or adjusted under 35 U.S.C. 154(b) by 0 days.

(21) Appl. No.: 16/532,199

(22) Filed: Aug. 5, 2019

(65) Prior Publication Data

US 2019/0352274 A1 Nov. 21, 2019

Related U.S. Application Data

(63) Continuation-in-part of application No. 16/002,022, filed on Jun. 7, 2018, now abandoned, which is a (Continued)

(51) Int. Cl.
*C07C 41/16* (2006.01)
*B01D 11/04* (2006.01)
(Continued)

(52) U.S. Cl.
CPC ........ *C07D 301/28* (2013.01); *B01D 11/0449* (2013.01); *B01D 11/0453* (2013.01);
(Continued)

(58) Field of Classification Search
CPC .. C07D 301/28; C07D 207/06; C07D 333/76; B01J 19/2495; B01J 14/00;
(Continued)

(56) References Cited

U.S. PATENT DOCUMENTS 3,228,877 A 1/1966 Mahon
3,640,980 A 2/1972 Baba
(Continued)

FOREIGN PATENT DOCUMENTS

CN 1643116 7/2005
CN 1826403 8/2006
(Continued)

OTHER PUBLICATIONS

Jackson et al., "Lipase-Cataclyzed Glycerolysis of Soybean oil in Supercritical Carbon Dioxide", JAOCS, vol. 74, No. 2, 1997, 4 pgs.
(Continued)

*Primary Examiner* — Joseph W Drodge
(74) *Attorney, Agent, or Firm* — Haynes and Boone, LLP

(57) ABSTRACT

An apparatus includes a conduit with two process fluid inlets at one end of the conduit, one process fluid outlet at an opposing end, a heat exchange medium inlet, and a heat exchange medium outlet. One of the fluid inlets includes a tube extending into the conduit and a perforated node at the end of the tube, and the other of the fluid inlets is arranged up stream of the perforated node. The apparatus further includes hollow tubes positioned longitudinally within the conduit between the two process fluid inlets, the process fluid outlet, the heat exchange medium inlet and the heat exchange medium outlet. In addition, the apparatus includes a collection vessel positioned proximate the fluid outlet and fibers extending through each of the hollow tubes, wherein one end of the fibers is secured to the perforated node and the other end of the fibers extends into the collection vessel.

12 Claims, 5 Drawing Sheets

Related U.S. Application Data continuation of application No. 14/876,992, filed on Oct. 7, 2015, now Pat. No. 10,189,806, which is a continuation of application No. 13/410,920, filed on Mar. 2, 2012, now Pat. No. 9,168,469, which is a continuation-in-part of application No. 12/576,407, filed on Oct. 9, 2009, now Pat. No. 8,128,825, which is a continuation-in-part of application No. 11/315,996, filed on Dec. 22, 2005, now Pat. No. 7,618,544.

(60) Provisional application No. 60/639,444, filed on Dec. 22, 2004.

(51) Int. Cl.
| | |
|---|---|
| C10L 1/02 | (2006.01) |
| C07C 41/14 | (2006.01) |
| C11C 3/14 | (2006.01) |
| C07C 67/03 | (2006.01) |
| B01J 19/24 | (2006.01) |
| B01J 14/00 | (2006.01) |
| C08L 71/02 | (2006.01) |
| C08G 59/02 | (2006.01) |
| C11C 3/10 | (2006.01) |
| C07D 301/28 | (2006.01) |
| C11C 3/04 | (2006.01) |

(52) U.S. Cl.
CPC ........... *B01J 14/00* (2013.01); *B01J 19/2415* (2013.01); *B01J 19/2475* (2013.01); *B01J 19/2495* (2013.01); *C07C 41/14* (2013.01); *C07C 41/16* (2013.01); *C07C 67/03* (2013.01); *C08G 59/022* (2013.01); *C08L 71/02* (2013.01); *C10L 1/026* (2013.01); *C11C 3/04* (2013.01); *C11C 3/10* (2013.01); *B01J 2219/00085* (2013.01); *B01J 2219/00599* (2013.01); *B01J 2219/24* (2013.01); *B01J 2219/3322* (2013.01); *C10L 2200/0476* (2013.01); *C10L 2270/026* (2013.01)

(58) Field of Classification Search
CPC ............... B01J 19/2415; B01J 19/2475; B01J 2219/3322; B01J 2219/00599; B01J 2219/24; B01J 2219/00085; B01J 19/248; B01J 19/24; B01J 2219/0089; B01J 2219/2423; B01J 2219/2401; B01J 2219/20; B01J 2219/201; C11C 3/04; C11C 3/10; C11C 41/14; C08G 59/022; C08L 71/02; C10L 1/026; C10L 2270/026; C10L 2200/0476; C07C 67/03; C07C 41/16; C07C 41/14; C07C 29/76; C07C 51/47; C07C 67/56; C07C 43/164; B01D 11/0449; B01D 11/04; B01D 11/0453; B01D 11/00; B01D 11/0415; B01D 63/02; B01D 63/024; B01D 63/025; B01D 63/026; B01D 63/04; B01D 69/00; B01D 69/02; B01D 69/08; B01D 71/00; B01D 71/06; B01D 71/26; B01D 71/28; B01D 71/30; B01D 71/32; B01D 71/34; B01D 71/36; B01D 71/38; B01D 71/40; B01D 71/42; B01D 71/44; B01D 71/46; B01D 71/48; B01D 71/50; B01D 71/52; B01D 71/54; B01D 71/56; B01D 71/58; B01D 71/60; B01D 71/62; B01D 71/64; B01D 2239/04; B01D 2239/4014; B01D 2239/0421; B01D 2239/0428; B01D 2239/0464; B01D 2239/0471; B01D 2239/0478; B01D 2239/0492; B01D 2239/065; B01D 2311/263; B01D 2311/2634; B01D 2311/2638; B01D 2313/04; C07F 9/09; C22B 3/0005; C02F 1/26; C02F 2101/203; C02F 2101/20; C02F 2101/308; C02F 2103/10; C02F 2101/24; C02F 2103/308; C02F 2101/34; C02F 2101/343; Y02P 10/234; Y02E 50/13
USPC ...... 210/257.2, 321.88, 321.89, 511, 500.23, 210/500.27, 500.35–500.43; 422/211, 422/212, 220, 608, 616, 617, 618
See application file for complete search history.

(56) References Cited

U.S. PATENT DOCUMENTS

| | | | |
|---|---|---|---|
| 3,754,377 | A | 8/1973 | Clonts |
| 3,758,404 | A | 9/1973 | Clonts |
| 3,839,487 | A | 10/1974 | Clonts |
| 3,977,829 | A | 8/1976 | Clonts |
| 3,992,156 | A | 11/1976 | Clonts |
| 4,130,549 | A | 12/1978 | Ueno et al. |
| 4,266,026 | A | 5/1981 | Breslau |
| 4,491,565 | A | 1/1985 | Verachtert |
| 4,532,347 | A | 7/1985 | Vaughan |
| 4,748,121 | A | 5/1988 | Beaver et al. |
| 4,753,722 | A | 6/1988 | Le et al. |
| 4,754,089 | A | 6/1988 | Matson et al. |
| 4,917,798 | A | 4/1990 | Liou et al. |
| 4,992,200 | A | 2/1991 | Lin et al. |
| 5,306,831 | A | 4/1994 | Beshouri et al. |
| 5,523,426 | A | 6/1996 | Jubin, Jr. et al. |
| 5,525,126 | A | 6/1996 | Basu et al. |
| 5,578,090 | A | 11/1996 | Bradin |
| 5,605,635 | A | 2/1997 | David |
| 5,705,074 | A | 1/1998 | Brient |
| 5,904,849 | A | 5/1999 | Kim et al. |
| 5,997,731 | A | 12/1999 | Suarez |
| 6,086,769 | A | 7/2000 | Kilambi et al. |
| 6,127,560 | A | 10/2000 | Stidham et al. |
| 6,132,491 | A | 10/2000 | Wai et al. |
| 6,139,723 | A | 10/2000 | Pelrine et al. |
| 6,174,501 | B1 | 1/2001 | Noureddini |
| 6,214,232 | B1 | 4/2001 | Baurmeister et al. |
| 6,238,566 | B1 | 5/2001 | Yoshida et al. |
| 6,245,304 | B1 * | 6/2001 | Jansen ............... B01J 8/22 210/321.8 |
| 6,271,023 | B1 * | 8/2001 | Baurmeister ........ B01D 53/22 210/321.64 |
| 6,300,431 | B1 | 10/2001 | Wang et al. |
| 6,303,830 | B1 | 10/2001 | Argyropoulos et al. |
| 6,309,550 | B1 * | 10/2001 | Iversen ............... B01D 53/22 210/644 |
| 6,350,419 | B1 | 2/2002 | Ho |
| 6,409,976 | B1 | 6/2002 | Poschmann et al. |
| 6,645,381 | B2 | 11/2003 | McEvoy |
| 6,887,304 | B2 | 5/2005 | Stroh et al. |
| 6,982,155 | B1 | 1/2006 | Fukuda et al. |
| 7,112,229 | B2 | 9/2006 | Khalil et al. |
| 7,153,996 | B2 | 12/2006 | Fagan et al. |
| 7,207,445 | B2 | 4/2007 | Manna et al. |
| 7,316,728 | B2 | 1/2008 | Parekh et al. |
| 7,459,084 | B2 | 12/2008 | Baig et al. |
| 7,618,544 | B2 | 11/2009 | Massingill, Jr. |
| 8,062,530 | B2 | 11/2011 | Schoen et al. |
| 8,092,656 | B2 | 1/2012 | Minnich et al. |
| 8,128,825 | B2 | 3/2012 | Massingill |
| 8,469,091 | B2 | 6/2013 | Bjorklund et al. |
| 8,980,100 | B2 | 3/2015 | Chidambaran |
| 9,085,471 | B2 | 7/2015 | Mandigo et al. |
| 9,168,469 | B2 | 10/2015 | Massingill |
| 9,738,553 | B2 | 8/2017 | Chidambaran et al. |
| 1,017,391 | A1 | 1/2019 | Chidambaran et al. |
| 1,018,980 | A1 | 1/2019 | Massingill |
| 2002/0003110 | A1 | 1/2002 | Rohrbach et al. |

(56) References Cited

U.S. PATENT DOCUMENTS

| | | |
|---|---|---|
| 2003/0012715 A1 | 1/2003 | Bond et al. |
| 2003/0219366 A1 | 11/2003 | Horwitz et al. |
| 2004/0144712 A1 | 7/2004 | Stroh et al. |
| 2006/0008392 A1 | 1/2006 | Graham et al. |
| 2006/0042158 A1 | 3/2006 | Lee |
| 2006/0157411 A1 | 7/2006 | Massingill |
| 2007/0004023 A1 | 1/2007 | Trachtenberg |
| 2007/0033863 A1 | 2/2007 | Butler |
| 2008/0300435 A1 | 12/2008 | Cortright et al. |
| 2010/0071260 A1 | 3/2010 | Massingill |
| 2010/0209982 A1 | 8/2010 | Basheer |

FOREIGN PATENT DOCUMENTS

| | | |
|---|---|---|
| CN | 101218005 | 7/2008 |
| CN | 101255348 | 9/2008 |
| EP | 0010466 | 4/1980 |
| EP | 0605173 | 7/1994 |
| EP | 1752770 | 2/2007 |
| EP | 2071015 | 6/2009 |
| EP | 2098553 | 9/2009 |
| EP | 2098556 | 9/2009 |
| GB | 2164663 | 3/1986 |
| JP | 4-71638 | 3/1992 |
| WO | WO 88/04286 | 6/1988 |
| WO | WO 2004/110602 | 12/2004 |
| WO | WO 2011/110967 | 9/2011 |

OTHER PUBLICATIONS

Schlosser et al., "Recovery and separation of organic acids by membrane-based solvent extraction and pertraction: An overview with a case study on recovery of MPCA," Separation and Purification Technology, vol. 41, 2005, pp. 237-266.

Sabolova et al., "Liquid-Liquid Equilibria of Butyric Acid in Water + Solvent Systems with Trioctylamine as Extractant," J. Chem Eng. Data, vol. 46, 2001, pp. 735-745.

Schlosser et al., "Three-phase contactor with distributed U-shaped bundles of hollow-fibers for pertration," Journal of Membrane Science, vol. 210, 2002, pp. 331-347.

Lazarova et al., "Application of large-scale hollow fiber membrane contactors for simultaneous extractive removal and stripping of penicillin G," Journal of Membrane Science, vol. 202, 2002, pp. 151-164.

Kragl et al., "Enzyme Catalysis in Ionic Liquids", Biotechnology, 2002, 7 pgs.

Earle et al., "Ionic liquids. Green solvents for the future," Pure Appl. Chem., vol. 72, No. 7, 2000, pp. 1391-1398.

Makosza, "Phase-transfer catalysis. A general green methodology in organic synthesis," Pure Appl. Chem., vol. 72, No. 7, 2000, pp. 1399-1403.

\* cited by examiner

FIBER CONDUIT REACTOR WITH A HEAT EXCHANGE MEDIUM INLET AND A HEAT EXCHANGE MEDIUM OUTLET

CONTINUING DATA

The present application is a continuation-in-part from U.S. patent application Ser. No. 16/002,022 filed Jun. 7, 2018, now abandoned, which is a continuation from U.S. patent application Ser. No. 14/876,992 filed Oct. 7, 2015, now U.S. Pat. No. 10,189,806, which is a continuation from prior U.S. patent application Ser. No. 13/410,920 filed Mar. 2, 2012, now U.S. Pat. No. 9,168,469, which is a continuation-in-part from prior U.S. patent application Ser. No. 12/576,407 filed Oct. 9, 2009, now U.S. Pat. No. 8,128,825, which is a continuation-in-part application from prior U.S. patent application Ser. No. 11/315,996 filed Dec. 22, 2005, now U.S. Pat. No. 7,618,544, which claims priority to U.S. Provisional Patent Application No. 60/639,444 filed Dec. 22, 2004.

GOVERNMENT FUNDING

This invention was made with support from the US Department of Agriculture, Phase II, Small Business Innovation Research No. 2006-33610-17174; National Science Foundation, Phase I, Small Business Technology Transfer Research Grant No. 2008-IIP-0740148; and National Science Foundation, Phase I, Small Business Technology Transfer Research Grant No. 2009-IIP-0924122.

FIELD OF THE INVENTION

This invention relates generally to fiber reactors/contactors to effect separation and reaction between two immiscible reaction components.

BACKGROUND OF THE INVENTION

The present invention enables the reaction between constituents of two immiscible fluids in order to produce desirable end products. This is currently achieved by making dispersions of one phase in the other to generate small droplets with a large surface area where mass transfer and reaction can occur, as described in Liquid-Liquid and Solid-Solid Systems, in Chemical Engineer's Handbook, 21-1-21-29, 5th ed., (Robert H. Perry & Cecil H. Chilton eds., McGraw-Hill 1973). Dispersions are used to wash water soluble impurities out of organic process streams, to neutralize organic process streams by extracting acid and base compounds from organic process streams, and to effect chemical reactions between components of two streams. For chemical reactions, phase transfer catalysts are frequently used to enhance mass transfer across the interface of the droplets, as described in Phase-Transfer Catalysis: Fundamentals, Applications, and Industrial Perspectives, (Charles M. Starks, Charles L. Liotta, & Marc Halpern eds., Chapman & Hall 1994). Co-solvents can also be used for this purpose.

Phase-transfer catalysis (PTC) technology is used in the commercial manufacture of more than $10 billion per year of chemicals, including monomers, additives, surfactants, polymers, flavors and fragrances petrochemicals, agricultural chemicals, dyes, rubber, pharmaceuticals, and explosives. PTC technology is also used in pollution prevention, pollution treatment and the removal or destruction of impurities in waste and product streams. PTC technology is used in these applications because it provides many compelling benefits, such benefits being primarily related to reducing the cost of manufacture of organic chemicals and pollution prevention. The many significant and advantageous process performance achievements which are routinely realized using PTC include increased productivity (increased yield, reduced cycle time, reduced or consolidated unit operations, and increased reactor volume efficiency), improved environmental performance (eliminated, reduced, or replaced solvent and reduced non-product output), increased quality (improved selectivity and reduced variability), enhanced safety (controlled exotherms and use of less hazardous raw materials), and reduced manufacturing costs (eliminated workup unit operations and use of alternative raw materials). With such a long list of highly desirable benefits achieved in commercial applications (usually multiple benefits are achieved in each application), it is no wonder that PTC technology is used in a wide variety of applications. Cost reduction and pollution prevention are the two most powerful driving forces in the chemical industry today, and they match precisely the strengths and benefits provided by PTC.

Despite these great benefits and the wide scope of applications, many chemical companies are still not using PTC technology. Probably the most difficult challenge to be met in the development stage of a PTC project is separation. Specifically, separation of phases can be difficult and time consuming since PTC catalysts resemble soaps and are interfacially active, and separation of catalysts after the reaction takes place is needed for product purity and quality.

Processing of vegetable oils typically includes the following steps: 1) acid degumming to remove phospholipids such as lecithin; 2) neutralization to remove free fatty acids that can cause rancidity in processed oils (in some processes degumming and neutralization are combined); 3) washing to remove residual caustic and soap in the neutralized vegetable oil (a double wash is often recommended); 4) bleaching to remove color bodies; and 5) deodorization. Moreover, many modern plant processes are continuous and use centrifuges to accelerate settling of oil and water layers in caustic neutralization and subsequent washing because of the formation of soap by reaction of free fatty acids and caustic, as in the PTC technology discussed above.

U.S. Pat. Nos. 3,754,377; 3,758,404; 3,839,487; 3,977,829; and 3,992,156 are directed to methods of effecting mass transfer between two immiscible fluids without forming dispersions.

U.S. Pat. No. 3,758,404 (issued to Clonts) discloses a method for effecting mass transfer between immiscible, concurrently flowing liquid-liquid phases, including a conduit having a bundle of elongated fibers positioned therein. The fiber bundle is positioned within the conduit at a perforated node that also acts as the point of introduction for the first liquid, which is deposited onto and within the fiber bundle as a film. A second liquid is directed into the conduit and over the first liquid deposited on the fibers. The large area of contact between the first and second liquids provides for an efficient mass transfer there between. The first liquid deposited on the fibers is moved along the fibers by the viscous drag occurring between the two concurrently flowing fluids. The first liquid in film form, sometimes referred to as the constrained phase, is moved along the fibers and eventually deposited in a collection vessel. The downstream end of the fiber bundle extends outwardly of the conduit into the collection vessel for the purpose of making direct fluid contact with fluid collected off of the bundle in order to prevent dispersion between the two phases. In this manner, mass transfer is efficiently effected between the two immiscible liquids without dispersion of one liquid into the other.

U.S. Pat. No. 3,754,377 (issued to Clonts) provides for a gas-liquid mass transfer process which is similar to the liquid-liquid mass transfer process just described. This patent teaches use of the fiber contactor to extract acidic components from natural gas and light hydrocarbons with aqueous caustic.

U.S. Pat. Nos. 3,839,487 and 3,977,829 (both issued to Clonts) describe use of the device disclosed therein for the alkylation of paraffin streams with olefin streams using concentrated sulfuric acid.

U.S. Pat. No. 3,992,156 (issued to Clonts) provides for mechanical improvements to fiber contactors, such as a method of supporting the fibers to prevent premature breakage and the use of multiple bundles of fibers and distribution tubes. These fiber contactors have proved to be remarkable inventions providing mass transfer at high efficiency levels without dispersion of one fluid into the other in the extraction of troublesome acidic impurities such as phenolics, hydrogen sulfide, $CO_2$, and mercaptan compounds from petroleum refinery process streams.

In addition, U.S. Pat. No. 5,705,074 (issued to Brient) teaches the use of fiber contactors to remove phenolics and other water-soluble organic materials from aqueous refinery waste streams by an extraction process. U.S. Pat. No. 5,997,731 (issued to Saurez) teaches the use of fiber contactors to neutralize an alkaline solution containing dissolved sodium sulfides, mercaptides and phenolates with a carbon dioxide-containing solvent and recover processable hydrocarbon values. U.S. Pat. No. 5,306,831 (issued to Beshouri, et al.) teaches use of fiber contactors to remove water soluble polyol impurities in a sorbitan ester mixture by treating a polyol-containing sorbitan ester dissolved in a solution containing a hydrocarbon and a polar organic solvent with an aqueous metal halide salt solution.

SUMMARY OF THE INVENTION

An apparatus for conducting chemical reactions and chemical extractions is provided, which includes a conduit comprising two process fluid inlets at one end of the conduit, one process fluid outlet at an opposing end of the conduit, a heat exchange medium inlet, and a heat exchange medium outlet. One of the two fluid inlets includes a tube extending into the conduit and a perforated node at the end of the tube, and the other of the two fluid inlets is arranged up stream of the perforated node. The apparatus further includes a plurality of hollow tubes positioned longitudinally within the conduit between the two process fluid inlets, the process fluid outlet, the heat exchange medium inlet and the heat exchange medium outlet. In addition, the apparatus includes a collection vessel positioned proximate the fluid outlet, the collection vessel having two fluid outlets respectively arranged along upper and lower portions of the collection vessel. Moreover, the apparatus includes a plurality of fibers extending through each of the plurality of hollow tubes, wherein one end of the plurality of fibers is secured to the perforated node, wherein the other end of the plurality of fibers extends into the collection vessel.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
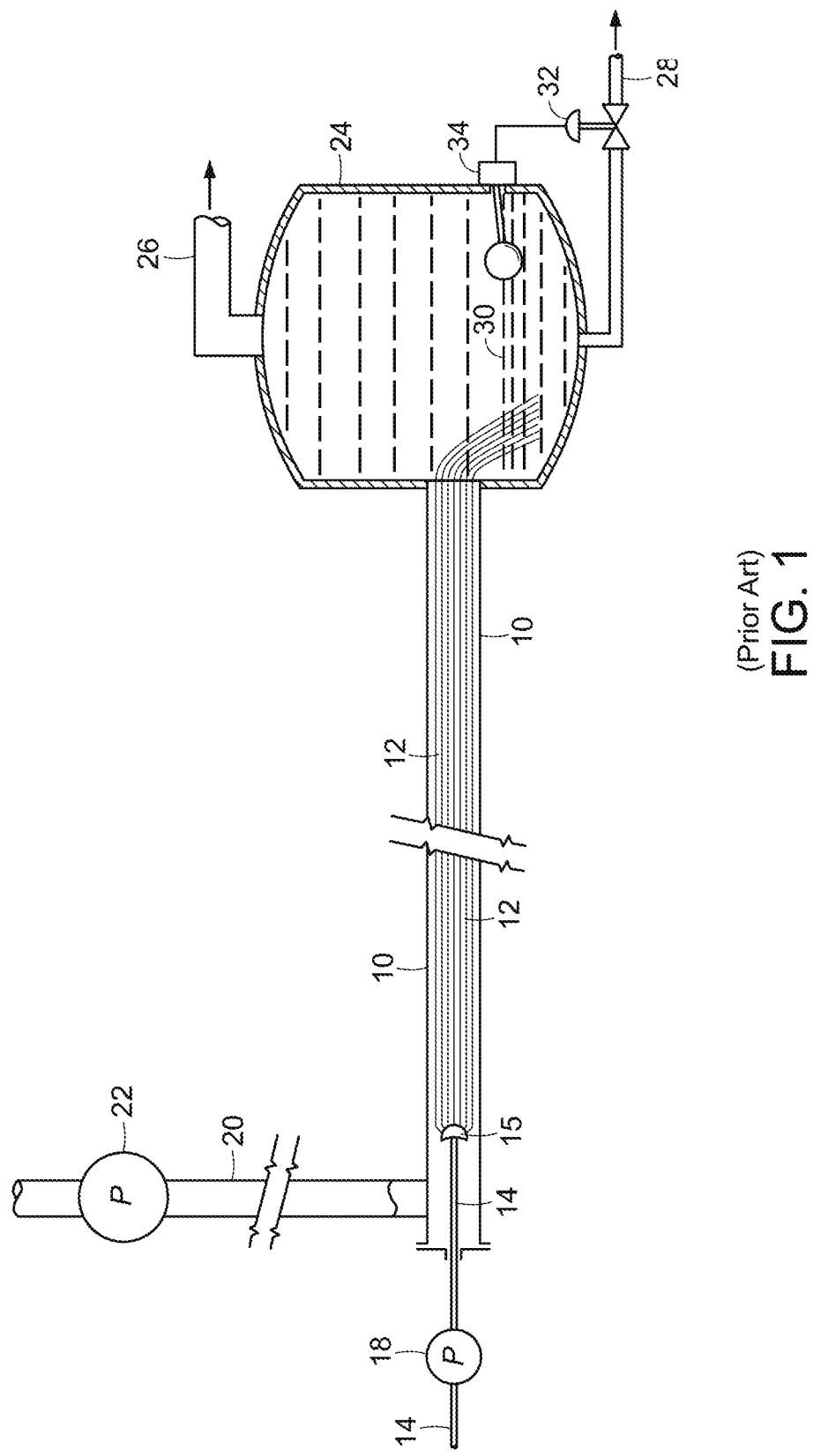
FIG. 1 illustrates a prior art example of a conduit reactor useful with the present invention.

The present invention is directed to (1) a new and improved process for effecting covalent chemical reactions between components of a first fluid that is initiated by component(s) of a second, substantially immiscible fluid, in order to produce a chemical product, (2) a new and improved process for neutralizing and washing organic reaction products and vegetable oils and fats prior to further processing, and (3) a new and improved process for degumming and neutralizing vegetable oils. Some embodiments of the present invention employ fiber reactors/contactors as described in U.S. Pat. Nos. 3,754,377; 3,758,404; and 3,992,156 which are incorporated herein by reference to the extent not inconsistent herewith; wherein two essentially immiscible fluids with reactive components in them, including one phase which preferentially wets the fibers of the contactor (referred to herein as the constrained phase) and another phase which flows between the fibers (referred to herein as the continuous phase), and, if needed, a phase transfer catalyst or a solvent that partially dissolves a reactant from the aqueous phase and brings it into the organic phase, are utilized. The conduit apparatuses described herein comprising fibers may be utilized as reactors and/or contactors/extractors, but for simplicity will be generally referred to as conduit reactors.

The fiber conduit reactor and phase transfer catalyzed reactions complement each other extremely well. In particular, a phase transfer catalyst can be employed to facilitate mass transfer across the interface between the phases. Co-solvents can also be used to enhance mass transfer across the interface of the phases, improving the rate of reaction in the fiber conduit reactor. A phase transfer catalyst may be introduced to the conduit reactor in the constrained phase, the continuous phase, or both phases. Phase transfer catalysts are generally selected based on their ability to be active at the interface of the phases and further to not produce emulsions that can cause the phases to be too difficult to separate. In addition, it is possible to tailor catalysts for reaction and for easy removal from the product. Useful phase transfer catalysts include, but are not limited to, quaternary ammonium compounds (e.g., a quaternary ammonium salt), quaternary phosphonium compounds (e.g., a quaternary phosphonium salt), sulfonium compounds, HTA-1, a phosphazenium salt, crown ethers, polyglycols (e.g., a polyethylene glycol, a polyethylene glycol ether, a polyethylene glycol ester), a hexaalkyl guanidinium salt, TDA-1, a lariat ether, a tertiary amine, and derivatives and/or combinations thereof.

One skilled in the relevant art would understand the applicability of various catalysts and reaction conditions to achieve a desired product. For example, high temperature phase transfer catalysts, such as but not limited to HTA-1

(Cognis) and phosphazenium salts, complement the conduit reactor's ability to operate conveniently at any temperature and pressure appropriate to a particular covalent chemical reaction being conducted. Moreover, because of the enhanced stability of the phosphazenium catalysts, the rates of chemical reactions employing phosphazenium catalysts can be increased merely by increasing the reaction temperature without destroying the catalyst. This can result in a reduction of reaction time of up to approximately 95% by changing the catalyst, temperature, pressure, and solvent. In any case, a phase transfer catalyst used in a fiber reactor may be bound to a polymer.

It is noted that the non-dispersive nature of the fiber conduit reactor broadens the number of compounds that may act as phase transfer catalysts to include all surfactants and surfactant-like compounds because they will not be agitated to form dispersions/emulsions that are difficult to separate. As such, utilizing surfactants in a fiber conduit reactor also works extremely well. In particular, surfactants may aid in the interaction of reactants at the interface between the constrained and continuous phases without being dispersed by the process, in effect enhancing mass transfer across the interface of the phases and improving the rate of reaction in the fiber conduit reactor. Either or both of the continuous and/or constrained streams may include a surfactant. Examples of surfactants which may be considered for use in a fiber conduit reactor include but are not limited to anionic surfactants, cationic surfactants, nonionic surfactants, and amphoteric surfactants. As used herein, an amphoteric surfactant refers to a surfactant that contains both an acid and a basic hydrophilic moiety in its surface.

Examples of anionic surfactants which may be used in a fiber conduit reactor include but are not limited to carboxylates, sulphonates (including but not limited to petroleum sulphonates, alkylbenzesulphonates, naphthalenesulphonates, and olefin sulphonates), sulphates (including but not limited to alkyl sulphates, sulphated natural oils and fats, sulphated esters, sulphated alkanolamides, and sulphated alkylphenols), and ethoxylated alkylphenols. Examples of cationic surfactants which may be used in a fiber conduit reactor include but are not limited to amines with amide linkages; polyoxyethylene alkyl and alicyclic amines; N,N,N',N' tetrakis substituted ethylenediamines; and 2-alkyl 1-hydroxyethyl 2-imidazolines. Examples of nonionic surfactants which may be used in a fiber conduit reactor include but are not limited to ethoxylated aliphatic alcohol, polyoxyethylene surfactants, carboxylic esters, polyethylene glycol esters, anhydrosorbitol ester and its ethyoxylated derivatives, glycol esters of fatty acids, carboxylic amides, monoalkanolamine condensates, and polyoxyethylene fatty acid amides. Examples of amphoteric surfactants which may be used in a fiber conduit reactor include but are not limited to N-coco 3-aminopropionic acid/sodium salt, N-tallow 3-iminodipropionate disodium salt, N-carboxylmethyl N-dimethyl N-9-octadecenyl ammonium hydroxide, and N-cocoamidethyl N-hydroxyethylglycine sodium salt.

Major advantages of the conduit reactor for producing new covalent chemical bonds by catalysis are: (1) processes are very fast because of excellent phase-to-phase contact, and (2) by-products are greatly reduced because dispersions and rag layers are virtually eliminated. Since dispersions are eliminated, settling time for coalescence of the dispersed particles is eliminated, thus reducing process time. When one of the reactants (such as epichlorohydrin or vegetable oil) can also react with water, this shorter contact time will mean better yields, reduced by-products, reduced pollution, and reduced costs for the process. Additionally, elimination of settling zones and/or tanks will reduce the footprint of the process and the cost and size of the process equipment.

The conduit reactor and vegetable oil processing also complement each other extremely well. Major advantages of the conduit reactor for degumming, neutralizing, washing, and/or bleaching fats, vegetable oils, and biodiesel are (1) very efficient degumming, neutralization, washing and bleaching because of excellent phase-to-phase contact, (2) fast separation of the two phases, and (3) elimination of long-lived dispersions caused by the soaps that form as result of caustic and water reacting with fatty acids. Use of co-solvents in the constrained phase is advantageous in light of the poor solubility of gums and stearate salts in water.

The fibers that may be employed in the conduit reactor include, but are not limited to, cotton, jute, silk, treated or untreated minerals, metals, metal alloys, treated and untreated carbon, polymers, polymer blends, and combinations thereof. Suitable treated or untreated minerals include, but are not limited to, glass, basalt, asbestos, ceramic, and combinations thereof. Suitable metals include, but are not limited to, iron, steel, nickel, copper, brass, lead, tin, zinc, cobalt, titanium, tungsten, nichrome, silver, aluminum, magnesium, and alloys thereof. Suitable polymers include, but are not limited to, hydrophilic polymers, polar polymers, hydrophilic copolymers, polar copolymers, and combinations thereof, such as polysaccharides, polypeptides, polyacrylic acid, polymethacrylic acid, polyhydroxyalkylesters of polyacids, functionalized polystyrene (including but limited to, sulfonated polystyrene and aminated polystyrene), polyphenolics, polynovolacs, nylon, polybenzimidazole, polyvinylidenedinitrile, polyvinylidene chloride, polyvinyl alcohols, polyethers, polyvinyl methyl ether, polyethyleneoxides, polyacids, polyamines, polyallylamines, polydiallyamines, polyethylenimine, polyoxazolines, polyphenylene sulfide, polymelamine, polyvinyl chloride, co-polyethyleneacrylic acid and ethylene-vinyl alcohol copolymers. The fibers can be treated for wetting with preferred phases and to protect from corrosion by the process streams. For instance, carbon fibers can be oxidized to improve wettability in aqueous streams and polymers can display improved wettability in aqueous streams by incorporation of sufficient functionality into the polymer, including but not limited to, hydroxyl, amino, acid, or ether functionalities.

The constrained phase can comprise any liquid that wets the fibers preferentially to the continuous phase, including but not limited to, such materials as water, water solutions, water and co-solvents, alcohols, phenols, amines (including but not limited to, polyamines, ethanolamines, and polyethanolamines), carboxylic acids, dimethyl sulfoxide, dimethyl formamide, sulfuric acid, ionic liquids (including but not limited to, 1-allyl-3-methylimidazolium chloride, 1-ethyl-3-methylimidazolium tetrafluoroborate, 1,2-dimethyl-3-n-propylimidazolium tetrafluoroborate, 1,2-dimethyl-3-n-butylimidazolium tetrafluoroborate, and 1,2-dimethyl-3-n-butylimidazolium hexafluorophosphate), and the like. Any of such materials may offer a solvent/reactant system that slightly compatibilizes both phases at their interface such that the two phases can react efficiently and be separated efficiently.

Referring to FIG. 1, which depicts the conduit reactor disclosed in U.S. Pat. No. 3,977,829, a conduit 10 has in it a bundle of elongated fibers 12 filling the conduit 10 for a portion of its length. These fibers 12 are secured to a tube 14 at a perforated node 16. Tube 14 extends beyond one end of conduit 10 and has operatively associated with it a metering pump 18 which pumps a first (constrained) phase liquid through tube 14 and onto fibers 12. Operatively connected to conduit 10 upstream of node 16 is an inlet pipe 20 having operatively associated with it a metering pump 22. This pump 22 supplies a second (continuous) phase liquid through inlet pipe 20 and into conduit 10, where it is squeezed between the constrained coated fibers 12. At the downstream end of conduit 10 is a gravity separator or settling tank 24 into which the downstream end of fibers 12 may extend. Operatively associated with an upper portion of gravity separator 24 is an outlet line 26 for outlet of one of the liquids, and operatively associated with a lower portion of gravity separator 24 is an outlet line 28 for outlet of the other liquid, with the level of an interface 30 existing between the two liquids being controlled by a valve 32, operatively associated with outlet line 28 and adapted to act in response to a liquid level controller indicated generally by the numeral 34.

In an alternative embodiment (not shown), an inverted arrangement using organophilic fibers with a constrained phase that is substantially organic can also be used. This arrangement can, for example, be used to extract organic materials from water with organic liquids constrained to the fibers.

During operation of an apparatus such as that depicted by FIG. 1, a liquid, such as a caustic aqueous solution, is introduced through tube 14 and onto fibers 12. Another liquid, such as epichlorohydrin containing resin chlorohydrin (organic phase), is introduced into conduit 10 through inlet pipe 20 and through void spaces (not labeled) between fibers 12. Fibers 12 will be wetted by the aqueous caustic solution preferentially to the organic mixture. The aqueous caustic solution will form a film (not shown) on fibers 12, wherein the film will be dragged downstream through conduit 10 by the passage of the organic mixture therethrough. Optionally, a phase transfer catalyst can be employed to facilitate mass transfer across the interface between the phases. Useful phase transfer catalysts for the reaction include, but are not limited to, quaternary ammonium compounds (e.g., a quaternary ammonium salt), quaternary phosphonium compounds (e.g., a quaternary phosphonium salt), sulfonium compounds, HTA-1, phosphazenium salts, crown ethers, polyglycols (e.g., a polyethylene glycol, a polyethylene glycol ether, a polyethylene glycol ester), a hexaalkyl guanidinium salt, TDA-1, a lariat ether, a tertiary amine and derivatives and/or combinations thereof. One skilled in the relevant art would understand the applicability of various catalysts and reaction conditions to achieve the desired product. The phase transfer catalyst may be introduced to the conduit reactor in the constrained phase, the continuous phase, or both phases. In addition, the phase transfer catalyst may be bound to a polymer. As a consequence of the relative movement of the organic phase with respect to the aqueous caustic film on fibers 12, a new interfacial boundary between the organic phase and the aqueous caustic solution is continuously being formed, and as a result, fresh resin chlorohydrin is brought in contact with caustic and the phase transfer catalyst, thus causing and accelerating the reaction.

Both liquid phases will be discharged into separator 24, but the volume of the organic phase discharged will be greater because the aqueous caustic solution will move at a slower velocity than the organic phase. In separator 24, the aqueous caustic solution will collect in the lower portion as it is heavier (denser) than the organic phase. Although the embodiment shown in FIG. 1 describes an arrangement wherein the downstream end of fibers 12 extends into separator 24, the present invention is not so limited. In some embodiments of the present invention, the downstream end of fibers 12 within separator 24 may be disposed above, below, or at the interface between the liquid phases within separator 24, depending on the relative density of the constrained phase and the continuous phase. Optionally, for denser constrained phases, the interface 30 within separator 24 can be kept at a level above the bottom of the downstream end of fibers 12, so that the heavier aqueous caustic film can be collected directly in the bottom of separator 24 without it being dispersed into the organic phase. Although the embodiment of the present invention disclosed above describes the use of a caustic solution as the aqueous phase and epichlorohydrin containing resin chlorohydrin as the organic phase, this example is only illustrative and the present invention is not so limited. Any suitable materials comprising substantially immiscible phases may be employed to practice the present invention.

The conduit reactor can be used with constrained phases lower in density than the continuous phase. Because the liquid phases come out of the conduit reactor separated and the constrained phase follows the fibers, the present invention may be utilized even when the phases are very close in density.

Figure 2:
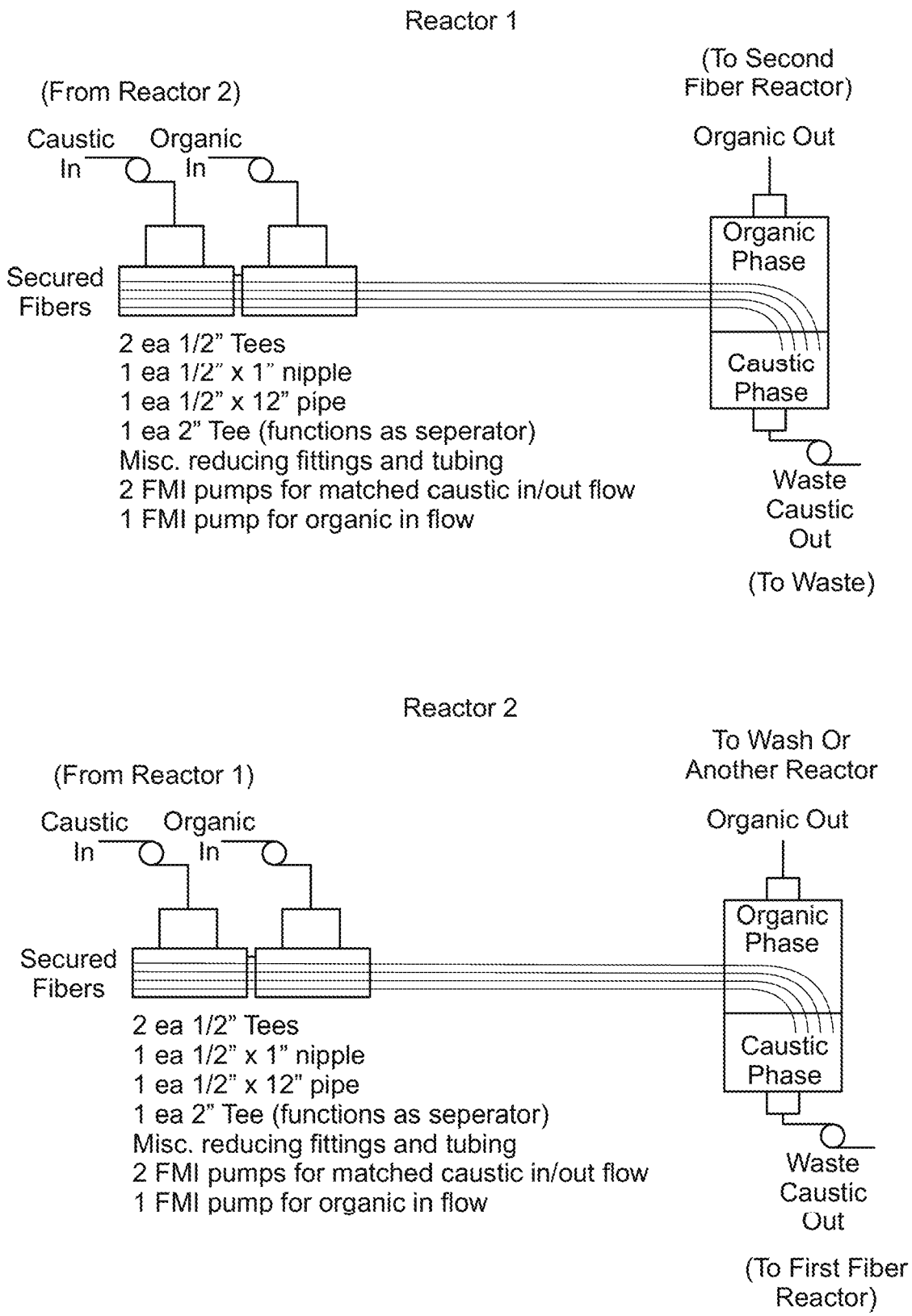
FIG. 2 depicts a conduit reactor system of the present invention.

FIG. 2 shows a conduit reactor system useful in practicing the present invention. In operation, the secured fibers in Reactors 1 and 2 are wetted by the constrained phase ("Caustic in") before the mobile phase ("Organic in") is started. FIG. 2 shows how multiple fiber reactors can be used to increase efficiency of utilization of reactants and to increase conversion of reactants by essentially feeding the liquids counter-currently through the reactor sequence. The continuous phase output of Reactor 1 ("Organic Out") is introduced to Reactor 2 ("Organic In") and further processed thereby. The constrained phase output of Reactor 2 is introduced to Reactor 1 ("Caustic In") while the constrained phase output of Reactor 1 is discarded as waste (or alternatively introduced to another reactor upstream of Reactor 1 (not shown)). In FIG. 2, the caustic and organic phases are depicted as flowing co-currently through each individual reactor, but the caustic and organic phases flow counter-currently through the reactor sequence. Of course, fresh caustic can be used with each reactor if desired.

Figure 3:
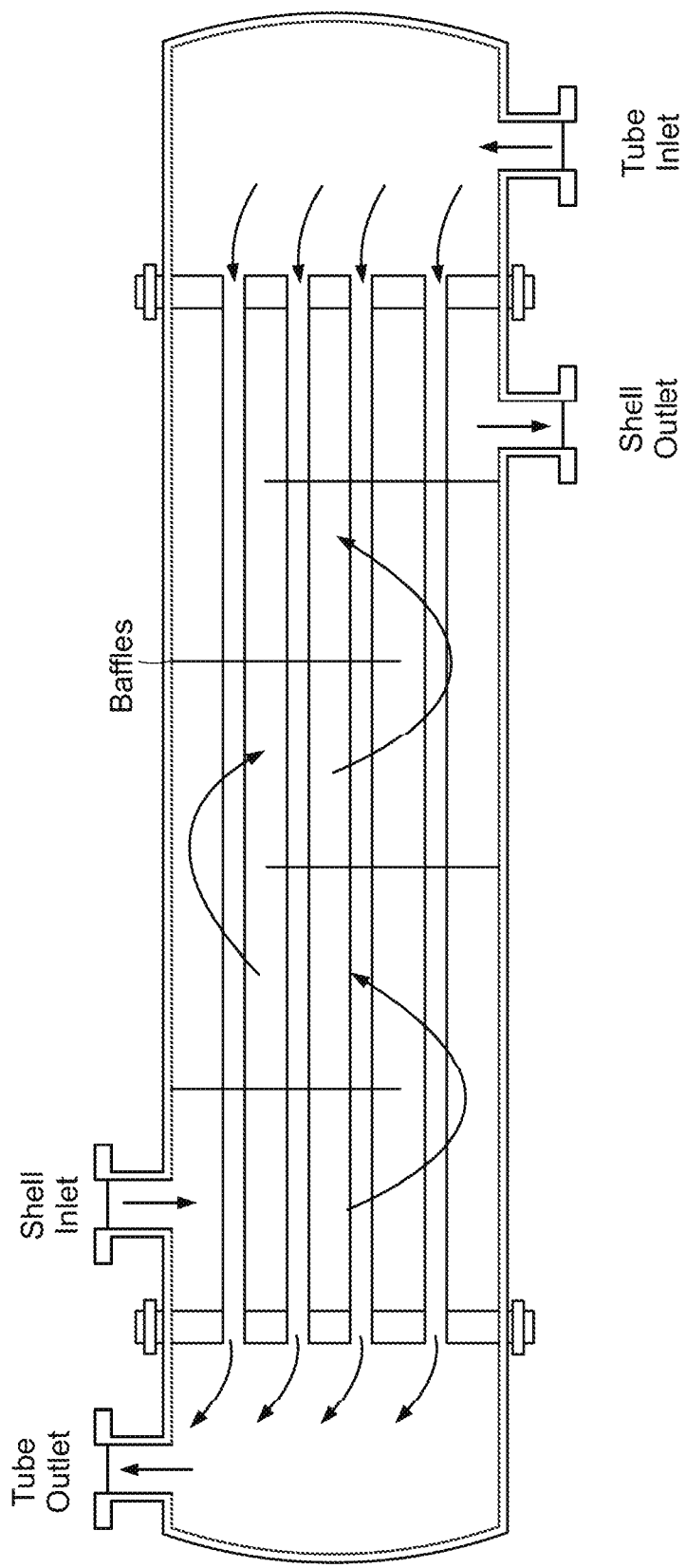
FIG. 3 depicts a shell and tube heat exchanger for incorporation into processes in accordance with some embodiments of the present invention.

FIG. 3 shows a conventional shell and tube heat exchanger. Combining this design with the conduit reactor yields a conduit reactor design adapted to handle exothermic reactions that need to be cooled and endothermic reactions that need to be heated. One can see that modification of the inlet of the heat exchanger tubes ("Tube Inlet") to duplicate the inlets shown in FIG. 1 would make each tube in the exchanger act like a thermally controlled fiber reactor. The exit end of the heat exchanger ("Tube Outlet") can be modified to operate as a separator to collect the aqueous phase on the bottom near the end of the fibers and allow the organic phase to exit from the top of the separator section. Introduction of a heat exchange medium to the exchanger (via "Shell Inlet") and outflow thereof (via "Shell Outlet") allows for the addition or removal of thermal energy from the exchanger tubes. While FIG. 3 depicts a counter-current flow heat exchanger, a co-current arrangement could also be used in conjunction with the present invention. In addition, although baffles are shown on the shell side of the exchanger in FIG. 3, the invention is not so limited and a heat exchanger without baffles may be employed.

Figure 5:
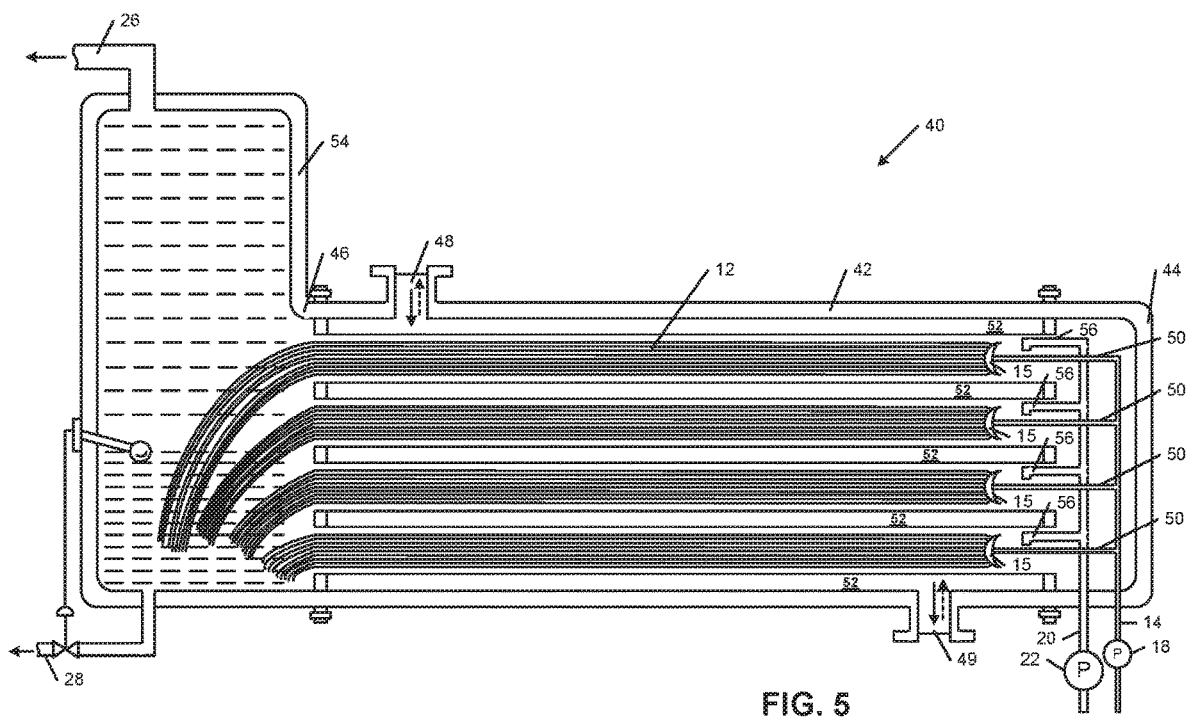
FIG. 5 depicts a fiber conduit reactor having a heat exchange medium inlet and a heat exchange medium outlet.

FIG. 5 illustrates an example conduit reactor having a heat exchange medium inlet and a heat exchange medium outlet as a result of combining the designs of the shell and tube heat exchanger illustrate in FIG. 3 and the conduit reactor shown in FIG. 1. In particular, in modifying the inlet of the heat exchanger tubes ("Tube Inlet") in FIG. 3 to duplicate the inlets shown in FIG. 1, FIG. 5 illustrates conduit reactor 40 having conduit 42 with two process fluid inlets near end 44 of the conduit. The two process fluid inlets respectively include tubes 14 and 20 each extending into conduit 42 and operatively associated with respective metering pumps 18 and 22. In addition, FIG. 5 illustrates conduit reactor 40 having supply pipes 50 extending from tube 14 and respectively into hollow tubes 52 which are longitudinally positioned within conduit 42 between ends 44 and 46 of conduit 42, and more specifically, between tubes 14 and 20 near end 44 and collection vessel 54 near end 46. Moreover, conduit reactor 40 includes perforated nodes 15 respectively coupled to the ends of supply pipes 50 in hollow tubes 52 as is similar to the configuration of the inlet comprising tube 14 and perforated node 15 in FIG. 1. In addition, conduit reactor 40 includes supply pipes 56 extending from tube 20 and respectively into hollow tubes 52 such that the ends of supply pipes 56 in the plurality of hollow tubes are arranged upstream of perforated nodes 15 as is similar to the configuration of inlet pipe 20 in FIG. 1.

In modifying the exit end of the heat exchanged ("Tube Outlet") in FIG. 3 to operate as a separator (to collect the aqueous phase on the bottom near the end of the fibers and allow the organic phase to exit from the top of the separator section), FIG. 5 illustrate conduit reactor 40 having collection vessel 54 proximate end 46 of conduit 42. As shown, collection vessel 54 includes fluid outlets 26 and 28 respectively arranged along upper and lower portions of the collection vessel similar to the configuration of gravity separator 24 in FIG. 1. Further similarity to the configuration of the conduit reactor depicted in FIG. 1, conduit reactor 40 includes a plurality of fibers 12 extending through each of hollow tubes 52, wherein on end of each set of fibers is secured to perforated node 15 in its respective hollow tube and the other end of each set of fibers extends into collection vessel 54. Moreover, FIG. 5 illustrates conduit 42 having heat exchange medium inlet 48 and heat exchange medium outlet 49 respectively near opposing ends of hollow tubes 52. More specifically, FIG. 5 illustrates heat exchange medium inlet 48 near the end of hollow tubes 52 proximate collection vessel 54 and, further, heat exchange medium outlet 49 near the end of hollow tubes proximate tubes 14 and 20 within conduit 42. Such a specific configuration facilitates a counter-current flow heat exchanger as is shown and described in reference to FIG. 3. In order to facilitate a co-current flow heat exchanger in conduit reactor 40, the positions of heat exchange medium inlet 48 and heat exchange medium outlet 49 may be switched, which is indicated by the dotted line arrows in the heat exchange medium passageways in and out of conduit 42 in FIG. 5.

Figure 4:
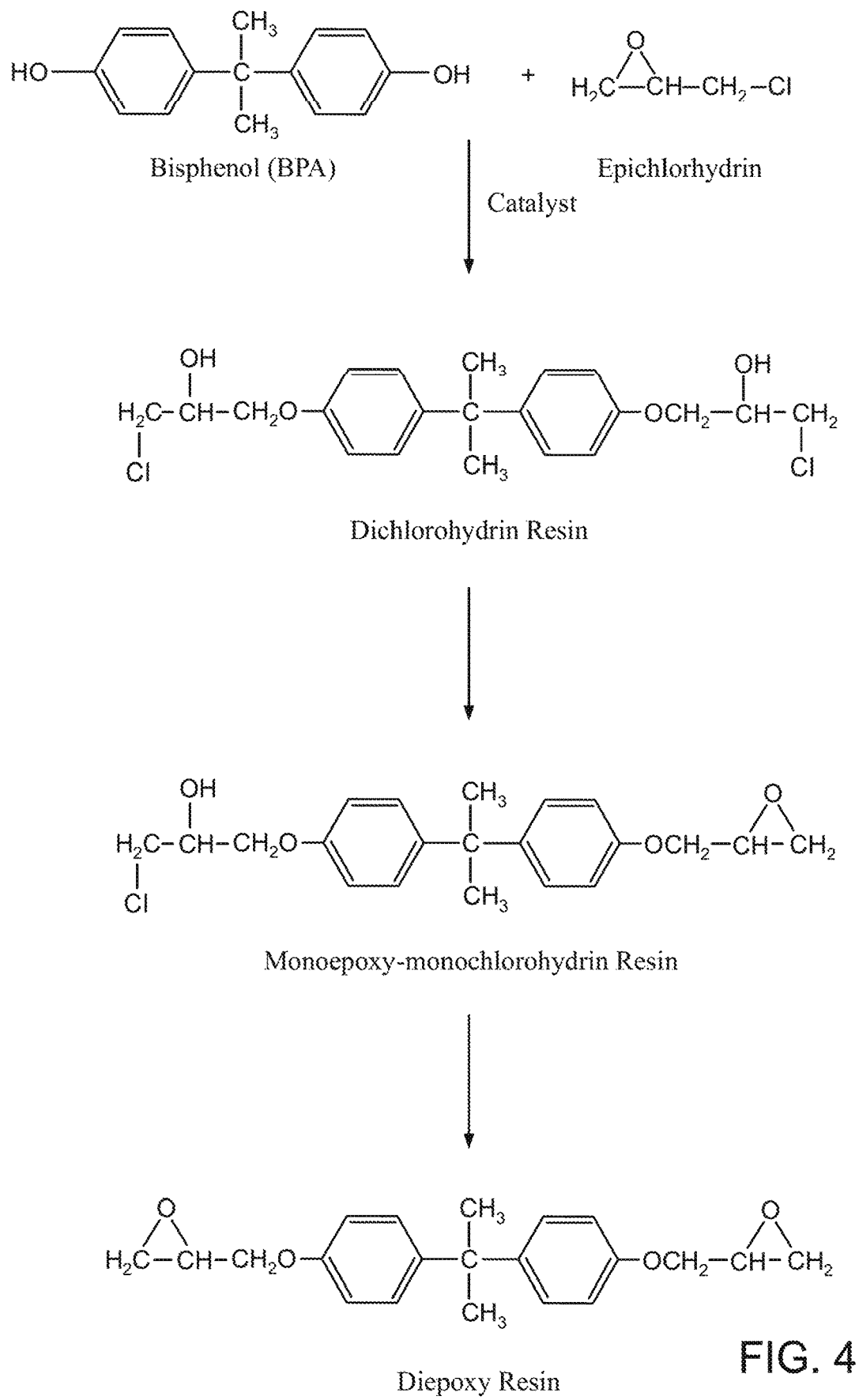
FIG. 4 illustrates a chemical synthesis of diepoxy resin that may be accomplished using various embodiments of the present invention.

FIG. 4 describes the chemical synthesis of diepoxy resin from epichlorohydrin and Bisphenol A (BPA). As illustrated therein, epichlorohydrin and BPA are combined in the presence of a basic material to produce a mixture of resin intermediates, diepoxy resin, and excess epichlorohydrin (not shown). While the major reaction products are described in FIG. 4, additional minor by-products typically produced are not shown. A large excess of epichlorohydrin is used to minimize formation of higher molecular weight products. Useful basic materials for the reaction include, but are not limited to, basic compounds such as amines (including but not limited to, ethanolamines, polyamines, and polyethanolamines), hydroxides, carbonates, bicarbonates, chlorides, phosphates, and combinations thereof. These basic materials may comprise cations including, but not limited to, lithium, sodium, potassium, calcium, quaternary complexes, and combinations thereof. The resin intermediates, dichlorohydrin resin and monoepoxy-monochlorohydrin resin (collectively referred to herein as "resin chlorohydrin"), are converted to the diepoxy resin (polyglycidyl ether resin) by subsequent exposure to an aqueous base and a phase transfer catalyst in the conduit reactor described in FIG. 1. While the reaction depicted by FIG. 4 utilizes epichlorohydrin and BPA, any suitable epihalohydrin and any suitable polyhydric alcohol may be used to produce polyglycidyl ether resins according to the present invention. One suitable polyhydric alcohol is phenol-novolac, (Bisphenol F) (available from Dow Deutschland GmbH & Co., Schwalbach, Germany).

The epichlorohydrin reaction described above is one example of a chemical reaction which could be achieved using the processes comprising the present invention. Other suitable reactions include, but are not limited to, O-alkylation (etherification), N-alkylation, C-alkylation, chiral alkylation, S-alkylation, esterification, transesterification, displacement (e.g., with cyanide, hydroxide, fluoride, thiocyanate, cyanate, iodide, sulfide, sulfite, azide, nitrite, or nitrate), other nucleophilic aliphatic & aromatic substitutions, oxidation, hydrolysis, epoxidation and chiral epoxidation, Michael addition, aldol condensation, Cannizzaro reaction, Henry reaction, Wittig condensation, Darzens Condensation, carbene reactions, thiophosphorylation, reduction, carbonylation, transition metal co-catalysis, Mannich reaction, Petasis reaction, Interrupted Feist-Benary reaction, N-heterocyclic carbomethoxylation, hydrogen-transfer reduction, decontamination reactions, HCl/HBr/HOCl/$H_2SO_4$ reactions, and polymer synthesis or polymer modification. In one aspect, an organic halide (R—X) and an organic acid (R'—H) may be coupled by the process described herein to produce a coupled product (R—R'), wherein R—X and R'—H can be on the same molecule or different molecules. In such an embodiment, the organic acid (R'H) may comprise a carbon acid, such as a cyclopentadiene, an acetoacetate, triphenylmethanes, xanthenes, thioxanthenes, benzoxazoles, fluorenes, indenes, malononitriles, trinitromethanes or an acetylene, or the organic acid may comprise carboxylic acids; thiocarboxylic acids; phenols, alcohols, thiols, amines, ethanolamines, and the like. In another aspect, water, alcohols, carboxylic acids, inorganic acids, thiols, amines, or the like may be reacted with an epoxide to form a glycol or a substituted glycol such as, but not limited to, an alkyl ether alcohol, an alkyl thioether alcohol, an ester alcohol, and an amino alcohol, a phosphate ester or a borate ester.

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention. In the examples provided, all temperature and pressure conditions should be considered as ambient unless otherwise noted.

Example 1

This example illustrates the use of a conduit reactor comprising a 12"×¼" stainless steel tube containing approximately 100,000 glass fibers.

Tests were run with approximately 100,000 glass fibers 17 inches in length in a ¼-inch internal diameter (I.D.) stainless steel tube. The liquid volume of this reactor was approximately 2.9 mL. Two liquids were pumped through this tube, with the constrained phase on the glass fibers being a 23% by weight sodium hydroxide aqueous solution. The continuous phase was a mixture of epichlorohydrin and resin chlorohydrin (made by reacting epichlorohydrin and bisphenol A (BPA) in a 10:1 molar ratio at 70° C. for 24 hours), and included 0.2% tetrabutyl ammonium hydroxide used as a coupling initiator and phase transfer catalyst. The caustic flow rate was 0.5 mL/min. Table 1 shows flow rate, stoichiometry, conversion, and contact time data obtained using the aforementioned reactor for phase transfer catalyzed ring closure of resin chlorohydrin to diepoxy resin.

TABLE 1

| Org. Flow (mL/min.) | NaOH:BPA | % Conversion | Contact Time (min.) |
|---|---|---|---|
| Start | 0 | 51.0 | 0 |
| 16 | 0.55 | 68.3 | 0.18 |
| 8 | 1.10 | 69.9 | 0.34 |
| 4 | 2.20 | 70.9 | 0.64 |
| 2 | 4.39 | 71.8 | 1.16 |
| 1 | 8.79 | 77.7 | 1.93 |
| 0.5 | 17.58 | 96.3 | 2.9 |

Example 2

This example illustrates the use of a conduit reactor comprising a 36".times.½" stainless steel tube with approximately 570,000 glass fibers.

Tests were run with approximately 570,000 glass fibers 40 inches in length in a ½-inch I.D. The liquid volume of this reactor was approximately 35 mL. Two liquids were pumped through this tube with the constrained phase on the glass fibers being a 23% by weight sodium hydroxide aqueous solution. The continuous phase was a mixture of epichlorohydrin and resin chlorohydrin (made by reacting epichlorohydrin and bisphenol A in a 10:1 molar ratio at 70° C. for 24 hours), with 0.1% tetrabutyl ammonium hydroxide coupling and phase transfer catalyst. The caustic solution was introduced onto the upstream end of the glass fibers at about 12 to about 60 mL per hour. The organic phase was introduced into the conduit and flowed past the fibers at rates varying between about 30 and about 3540 mL per hour. After passing through the fiber reactor, the separated organic phase was analyzed by gel permeation chromatography (GPC) for resin and chlorohydrin content and the results shown as percent conversion to diepoxy resin as listed in Table 2.

TABLE 2

| Run | Org. Flow (mL/min.) | Aq. Flow (mL/hr) | % PTC | % Conversion | Contact Time (min.) |
|---|---|---|---|---|---|
| 1 | 30 | 30 | 0.1 | 95.7 | 35 |
| 2 | 60 | 30 | 0.1 | 94.7 | 23 |
| 3 | 120 | 30 | 0.1 | 92.9 | 12.8 |
| 4 | 240 | 30 | 0.1 | 87.9 | 7.1 |
| 5 | 480 | 30 | 0.1 | 77.3 | 3.76 |
| 6 | 210 | 30 | 0.1 | 98.45 | 23.3 |
| 7 | 330 | 30 | 0.1 | 99.09 | 5.8 |
| 8 | 950 | 30 | 0.1 | 96.60 | 2.1 |
| 9 | 480 | 30 | 0.1 | 98.08 | 4.1 |
| 10 | 2010 | 30 | 0.1 | 88.2 | 1.0 |
| 11 | 1290 | 30 | 0.1 | 92.2 | 1.6 |
| 12 | 2480 | 30 | 0.1 | 82.2 | 0.8 |
| 13 | 3540 | 30 | 0.1 | 79.4 | 0.6 |
| 14 | 2940 | 30 | 0.1 | 82.7 | 0.7 |
| 15 | 1830 | 60 | 0.1 | 90.1 | 1.1 |
| 16 | 1800 | 40 | 0.1 | 92.8 | 1.14 |
| 17 | 1800 | 20 | 0.1 | 90.8 | 1.15 |
| 18 | 1200 | 12 | 0.1 | 90.7 | 1.7 |
| 19 | 240 | 12 | 1.0 | 98.5 | 8.3 |

Example 3

This example illustrates the use of a conduit reactor comprising a 12".times.½" stainless steel tube with approximately 570,000 glass fibers.

Tests were run with approximately 570,000 glass fibers 16 inches in length in a 12" outside diameter (O.D.)×½-inch I.D. stainless steel tube. The liquid volume of this reactor was approximately 18 mL. Two liquids were pumped through this tube with the constrained phase on the glass fibers being a 23% by weight sodium hydroxide aqueous solution containing 2% tetrabutyl ammonium hydroxide phase transfer catalyst. The continuous phase was a mixture of benzyl alcohol and benzyl bromide (1:1 molar ratio) in equal weight of toluene. The caustic solution was introduced onto the upstream end of the glass fibers at 60 mL/hr. The organic phase was introduced into the conduit and flowed past the fibers at rate of 270 mL/hr. The reactor was maintained at 75° C. After passing through the fiber reactor, the organic phase separated cleanly from the aqueous phase and was analyzed by gas chromatography-mass spectroscopy (GC-MS). The data, shown in Table 3 below, indicate about 70% conversion of benzyl alcohol to benzyl ether in 3.25 minutes reaction time, with no settling time required.

TABLE 3

| Component | Relative Concentration (GC-MS) |
|---|---|
| Benzyl bromide | 10 |
| Benzyl alcohol | 17 |
| Benzyl ether | 72 |

Example 4

The same conduit reactor used in Example 3 above was used in this experiment. Two liquids were pumped through the reactor with the constrained phase on the glass fibers being an aqueous solution comprising about 94% methanol, 4% sodium hydroxide, and 2% water. The continuous phase was soybean oil. The methanolic caustic solution was introduced onto the upstream end of the glass fibers at 60 mL/hr. The soybean oil was introduced into the conduit and flowed past the fibers at a rate of 270 mL/hr. The reactor was maintained at 60° C. After passing through the fiber reactor, the organic phase separated cleanly from the aqueous phase and was analyzed by gas chromatography (GC). The data, shown in Table 4 below, indicate about 67% conversion of vegetable oil to fatty acid alkyl ester (biodiesel) in 5 minutes reaction time, with no settling time required.

TABLE 4

| Component | Relative Concentration (GC Area Percent) |
|---|---|
| Soybean oil | 33 |
| Biodiesel | 67 |

Example 5

This example illustrates the use of a conduit reactor comprising a 96"×½" stainless steel tube with approximately 360,000 twenty-two micron stainless steel fibers and a liquid volume of approximately 166 mL. Two liquids were pumped through the reactor with the constrained phase on the stainless steel fibers being a solution comprising about 94.25% methanol, about 3.75% sodium hydroxide, and about 2.1% water. The continuous phase was soybean oil. The methanolic caustic solution was introduced onto the upstream end of the stainless steel fibers at approximately 112.8 mL/hr. The soybean oil was introduced into the conduit and flowed past the fibers at a rate of approximately 420 mL/hr. The mole ratio of methanol:oil was 6:1 with approximately 0.78% NaOH by weight of oil. The reactor was maintained at approximately 75° C. After passing through the fiber reactor, the organic phase separated cleanly from the aqueous phase and was analyzed by gel permeation chromatography (GPC). The data, shown in Table 5 below, indicate >99% conversion of vegetable oil to fatty acid alkyl ester (biodiesel) in approximately 22 minutes reaction time. A mass balance indicated approximately 2% oil was hydrolyzed to FFA by approximately 2% water in the system. System pressure was approximately 45 psig.

TABLE 5

| Component | Relative Concentration (GPC Area Percent) |
|---|---|
| Triglyceride | undetectable |
| Diglyceride | 0.19 |
| Monoglyceride | 0.77 |
| Biodiesel | 99.06 |

Example 6

The same conduit reactor used in Example 3 above was used in this experiment. Two liquids were pumped through the reactor with the constrained phase on the glass fibers being a 5% sodium hydroxide solution. The continuous phase was commercial degummed soybean oil containing 0.13% free fatty acid (FFA) (available from Archer Daniels Midland Company, Decatur, Ill.) dissolved at 30% by weight in hexane. This simulated miscella was neutralized as the 5% caustic solution was flowed through the reactor at a rate of 1 mL/min. The neutralization results, shown in Table 6 below, indicate that FFA concentrations more than ten times lower than the 0.05% FFA specification for commercial soybean oil were obtained. This exceptional FFA reduction was achieved in 1 to 3 minutes with excellent and immediate separation of the phases. The reactor pressure did rise over time, however, indicating that solids were building up in the reactor thereby restricting flow (i.e., reactor plugging).

TABLE 6

| Run | Org. Flow Rate (mL/min.) | Residual FFA (%) | Contact Time (min.) | Time before plugging observed |
|---|---|---|---|---|
| 1 | 4.5 | 0.0018 | 3.3 | 1 day |
| 2 | 9 | 0.0020 | 1.8 | 6-8 hr. |
| 3 | 12 | 0.0027 | 1.4 | 3-4 hr. |
| 4 | 16 | 0.0026 | 1.1 | <1 hr. |

Example 7

The same conduit reactor used in Example 3 above was used in this experiment. Two liquids were pumped through the reactor with the constrained phase on the glass fibers being an aqueous ethanolic sodium hydroxide solution. The ethanol:water ratio was varied from about 1:9 to about 9:1. The continuous phase used was soybean oil dissolved at 30-95% by weight in hexane. The soybean oil used was retail soybean oil contaminated with about 1% FFA to about 16% FFA. The ethanol was included to prevent reactor plugging, which occurred in Example 5 caused by organic salts (sodium carboxylates) forming and precipitating during the reaction. The reactor was maintained at 25° C. or 70° C. to increase solubility of sodium carboxylate salts. Reactor pressure remained low at ethanol:water ratios at or above about 3:7. Results are shown in Table 7 below. Runs made using 10% and 20% ethanol co-solvent (not shown in Table 7) gave pressure increases, indicating only partial solubility of sodium carboxylates at these high levels of free fatty acids. During run 8, which utilized a high caustic and high FFA concentration, solids were observed but the reactor did not plug.

TABLE 7

| Run | Temp. (° C.) | NaOH (%) | EtOH (%) | Aq. Flow (mL/min.) | Org. Flow (mL/min.) | % Oil in Micella | % FFA in Oil | % FFA in Effluent | NaOH:FFA Ratio | % FFA Removal | Contact Time (min.) |
|---|---|---|---|---|---|---|---|---|---|---|---|
| 1 | 25 | 1 | 30 | 3 | 3 | 30 | 1.67 | 0.01 | 19.56 | 97.88 | 3.00 |
| 2 | 25 | 1 | 30 | 1 | 9 | 30 | 1.67 | 0.01 | 2.17 | 98.48 | 1.80 |
| 3 | 25 | 0.58 | 60 | 1 | 16 | 30 | 1.00 | 0.01 | 1.10 | 99.18 | 1.06 |
| 4 | 70 | 1 | 60 | 1 | 8 | 95 | 1.00 | 0.28 | 1.20 | 71.99 | 2.00 |
| 5 | 70 | 0.95 | 60 | 1 | 8 | 90 | 1.00 | 0.01 | 1.20 | 98.60 | 2.00 |
| 6 | 70 | 0.95 | 60 | 1 | 8 | 85 | 1.00 | 0.00 | 1.27 | 99.80 | 2.00 |
| 7 | 25 | 10 | 90 | 1 | 9 | 30 | 16.67 | 0.05 | 1.97 | 99.07 | 1.80 |
| 8 | 25 | 12.5 | 90 | 1 | 16 | 30 | 16.67 | 0.01 | 1.40 | 99.87 | 1.06 |

Example 8

The same conduit reactor used in Example 3 was used in this experiment. Two liquids were pumped through the reactor with the constrained phase on the glass fibers being aqueous ethanol containing about 1.73% sodium hydroxide. The ethanol:water ratio employed in Runs 1 and 2 was 3:2, and in Run 2 95% ethanol was used. The continuous phase used was neat soybean oil containing about 1% free fatty acids. The reactor was maintained at about 70° C. The reactor pressure varied from about 150 psig to about 500 psig with a flow of oil of about 4 mL/min. to about 8 mL/min., providing for a contact time of about 2 minutes to about 3.6 minutes in the reactor. The fiber contactor provided about 90% removal of FFA in this time frame. The FFA content of the exit oil was about 0.1%. The results are shown in Table 8. A longer contact time would presumably be needed to get the FFA level down to <0.05% under these reaction conditions, which produce a viscous fluid environment in the reactor.

TABLE 8

| Run | NaOH (%) | EtOH (%) | Aq. Flow (mL/min.) | Org. Flow (mL/min.) | NaOH:FFA Ratio | FFA Removal (%) | Contact Time (min.) |
|---|---|---|---|---|---|---|---|
| 1 | 1.73 | 60 | 1 | 4 | 3.28 | 90.2 | 3.6 |
| 2 | 1.73 | 60 | 1 | 8 | 1.64 | 87.7 | 2.0 |
| 3 | 1 | 95 | 1 | 4 | 1.73 | 77.9 | 3.6 |

Example 9

The same conduit reactor used in Example 3 was used in this experiment. Two liquids were pumped through the reactor with the constrained phase on the glass fibers being water, and the organic phase comprising commercial biodiesel fuel (available from Archer Daniels Midland Company, Decatur, Ill.). The phases separated quickly and easily at 1 minute contact time with minimal pressure, thereby demonstrating excellent washing characteristics, as shown in Table 9 below.

TABLE 9

| Biodiesel Flow Rate (mL/min.) | H2O Flow Rate (mL/min.) | Pressure (PSIG) | Observations |
|---|---|---|---|
| 8 | 1 | 0 | Clear with good separation |
| 12 | 1 | 0 | Clear with good separation |
| 16 | 1 | 0 | Clear with good separation |
| 16 | 0.5 | 5-8 | Clear with good separation |

Example 10

This example illustrates extraction using a conduit reactor comprising a 108"×½" stainless steel tube with approximately 360,000 twenty-two micron stainless steel fibers and a liquid volume of approximately 187 mL. Two liquids were pumped through the reactor with the constrained phase on the stainless steel fibers being an extraction solution comprising about 15% water, about 84% ethanol (having a 95% concentration level), and about 1% superphosphoric acid. The continuous phase was cottonseed oil miscella (30% oil in hexane) containing about 1400 ppm phosphorous. The ethanol in the constrained phase was used to keep the free fatty acids in the cottonseed oil soluble to prevent the conduit reactor from plugging. The extraction solution was introduced onto the upstream end of the stainless steel fibers at approximately 62 mL/min. The cottonseed oil miscella was introduced into the conduit and flowed past the fibers at a rate of approximately 106 mL/min. The reactor was maintained at approximately 75° C. After passing through the fiber reactor, the organic phase separated cleanly from the aqueous phase. The hexane was evaporated and the gum content of the cottonseed oil was analyzed by hot water precipitation (none visible) and contained 3 ppm phosphorous, meaning 1397 ppm phosphorous was removed from the cottonseed oil. System pressure was approximately 15 psig. About 0.18% cottonseed oil was extracted with the gums. The water in the constrained phase was used to reject the cottonseed oil so very little oil was extracted with the gums.

It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed:

1. An apparatus for conducting chemical reactions and chemical extractions, the apparatus comprising:
   a conduit comprising:
      two process fluid inlets near a first end of the conduit, wherein each of the two process fluid inlets comprises a tube extending into the conduit;
      a heat exchange medium inlet; and
      a heat exchange medium outlet;
   a collection vessel position proximate a second end of the conduit opposing the first end, wherein the collection vessel comprises two fluid outlets respectively arranged along upper and lower portions of the collection vessel;
   a plurality of hollow tubes positioned longitudinally within the conduit between the tubes of the two process fluid inlets extending in the conduit and the collection vessel, wherein the heat exchange medium inlet of the conduit is near one end of the hollow tubes, and wherein the heat exchange medium outlet of the conduit is near an opposing end of the hollow tubes;
   distinct sets of fibers respectively extending through the plurality of hollow tubes, wherein one end of each of the distinct sets of fibers is secured to a respective perforate node arranged in the hollow tube through which the respective distinct set of fibers extends, and wherein the other end of each distinct set of fibers extends into the collection vessel.

2. The apparatus of claim 1, further comprising:
   a first set of supply pipes extending from the tube of one of the two process fluid inlets and respectively into the plurality of hollow tubes;
      wherein the perforated nodes are respectively coupled to the ends of the first set of supply pipes in the plurality of hollow tubes; and
   a second set of supply pipes extending from the tube of the other of the two process fluid inlets and respectively into the plurality of hollow tubes such that the ends of the second set of supply pipes in the plurality of hollow tubes are arranged between the perforated nodes and the first end of the conduit.

3. The apparatus of claim 1, wherein the heat exchange medium inlet is near an end of the hollow tubes which is proximate the collection vessel, and wherein the heat exchange medium outlet is near an end of the hollow tubes which is proximate the tubes of the two process fluid inlets.

4. The apparatus of claim 1, wherein the heat exchange medium inlet is near an end of the hollow tubes which is proximate the tubes of the two process fluid inlets, and wherein the heat exchange medium outlet is near an end of the hollow tubes which is proximate the collection vessel.

5. The apparatus of claim 1, wherein the distinct sets of fibers are hydrophilic fibers comprising materials selected from the group consisting of treated or untreated minerals, metals, metal alloys, treated and untreated carbon, polymers, and polymer blends.

6. The apparatus of claim 5, wherein the hydrophilic fibers comprise treated or untreated minerals comprising materials selected from the group consisting of glass, basalt, asbestos, ceramic, and combinations thereof.

7. The apparatus of claim 5, wherein the hydrophilic fibers comprise metals comprising materials selected from the group consisting of iron, steel, nickel, copper, brass, lead, tin, zinc, cobalt, titanium, tungsten, nichrome, silver, aluminum, magnesium, and combinations and alloys thereof.

8. The apparatus of claim 5, wherein the hydrophilic fibers comprise polymers comprising materials selected from the group consisting of hydrophilic polymers, polar polymers, hydrophilic copolymers, polar copolymers, and combinations thereof.

9. The apparatus of claim 8, wherein the polymers comprise materials selected from the group consisting of polysaccharides, polypeptides, polyacrylic acid, polymethacrylic acid, polyhydroxyalkylesters of polyacids, functionalized polystyrene, polyphenolics, polynovolacs, nylon, polybenzimidazole, polyvinylidenedinitrile, polyvinylidene chloride, polyvinyl alcohols, polyethers, polyvinyl methyl ether, polyethyleneoxides, polyacids, polyamines, polyallylamines, polydiallyamines, polyethylenimine, polyoxazolines, polyphenylene sulfide, polymelamine, polyvinyl chloride, co-polyethylene-acrylic acid, and ethylene-vinyl alcohol copolymers.

10. The apparatus of claim 1, wherein the distinct sets of fibers comprise functionalized fibers.

11. The apparatus of claim 1, wherein the distinct sets of fibers comprise solid fibers.

12. The apparatus of claim 1, wherein the distinct sets of fibers comprise hollow fibers.

* * * * *